United States Patent [19]

Ahjopalo et al.

[11] 4,266,131
[45] May 5, 1981

[54] GAS ANALYZER

[75] Inventors: Hannu Ahjopalo, Vantaa; Jorma J. Auvinen, Nummela, both of Finland

[73] Assignee: Instrumentarium OY, Helsinki, Finland

[21] Appl. No.: 71,564

[22] Filed: Aug. 31, 1979

[30] Foreign Application Priority Data

Sep. 1, 1978 [FI] Finland .................................. 782692

[51] Int. Cl.³ ............................................ G01N 21/26
[52] U.S. Cl. .................................. 250/341; 250/345; 356/437
[58] Field of Search .................. 250/343, 344, 345; 356/51, 433, 436, 437

[56] References Cited

U.S. PATENT DOCUMENTS

| 3,116,413 | 12/1963 | Schaefer et al. ..................... 250/345 |
| 3,193,676 | 7/1965 | Smart .................................. 250/345 |
| 4,157,470 | 6/1979 | Kotaka et al. ....................... 250/345 |

Primary Examiner—Davis L. Willis
Attorney, Agent, or Firm—Andrus, Sceales, Starke & Sawall

[57] ABSTRACT

The present invention concerns a gas analyzer, for instance a $CO_2$ analyzer, comprising a measuring chamber for the gas to be examined, a reference chamber from which the gas to be measured has been drawn off, a light source and a chopper disk, which chops the light beam to make it pass alternatingly through the measuring and reference chambers and so that in between there is a period during which no light is passed through at all, and an automatic gain control which maintains a constant difference between the "dark" signal and the signal delivered by the reference chamber. An attenuation member is positioned adjacent the reference chamber so the light beam passing through the reference chamber is attenuated to cause a shift of the operating point of the gain control circuit into the gently ascending part of the absorption versus concentration curve.

5 Claims, 2 Drawing Figures

GAS ANALYZER

BACKGROUND OF THE INVENTION

The problem in gas analyzers of this type known in the art is that as the light has to travel a certain distance through ambient gas an error is introduced by variations of the content of the gas under measurement in the ambient gas. The magnitude of this error is dependent on the ambient content, on the distance which the light beam travels in the ambient space and the content of the gas under measurement. In a $CO_2$ analyzer, for instance, where the measuring light beam travels part of its path in the ambient $CO_2$ content, the varying ambient $CO_2$ content introduces an error. This problem is accentuated particularly in $CO_2$ analyzers for the reason that the absorption of infra-red radiation as a function of $CO_2$ content is strongly non-linear. The ambient carbon dioxide causes equal attenuation both of the measuring and the reference beam. Since in the case of increasing $CO_2$ content the absorption caused by it increases at a relatively slower rate, that is, the absorption curve plotted as a function of content becomes less steep at the upper end, even a minor additional absorption causes a major error. This is only minimally corrected by the change in gain which is caused by the attenuation of the reference beam due to the ambient environment.

SUMMARY OF THE INVENTION

The object of the invention is to improve a gas analyzer of the type mentioned so that the said error effect can be substantially reduced.

This aim is achieved, as taught by the invention, in that in the path of the light beam passing through the reference chamber an attenuation member has been placed which provides a high enough attenuation in the wavelength range employed, to cause a shift of the operating point of the gain control circuit into the gently ascending part of the absorption vs. content curve. Hereby the additional attenuation caused by the ambient environment in the reference beam results in a change of gain which compensates for the ambient attenuation of the measuring beam.

It is advantageous in the measuring ranges normally concerned to CO analyzers if the attenuation of the attenuation disk is on the order of 8%.

In the following, an embodiment example of the invention shall be more closely described with reference to the attached drawings, wherein:

DESCRIPTION OF THE PREFERRED EMBODIMENT

Figure 1:
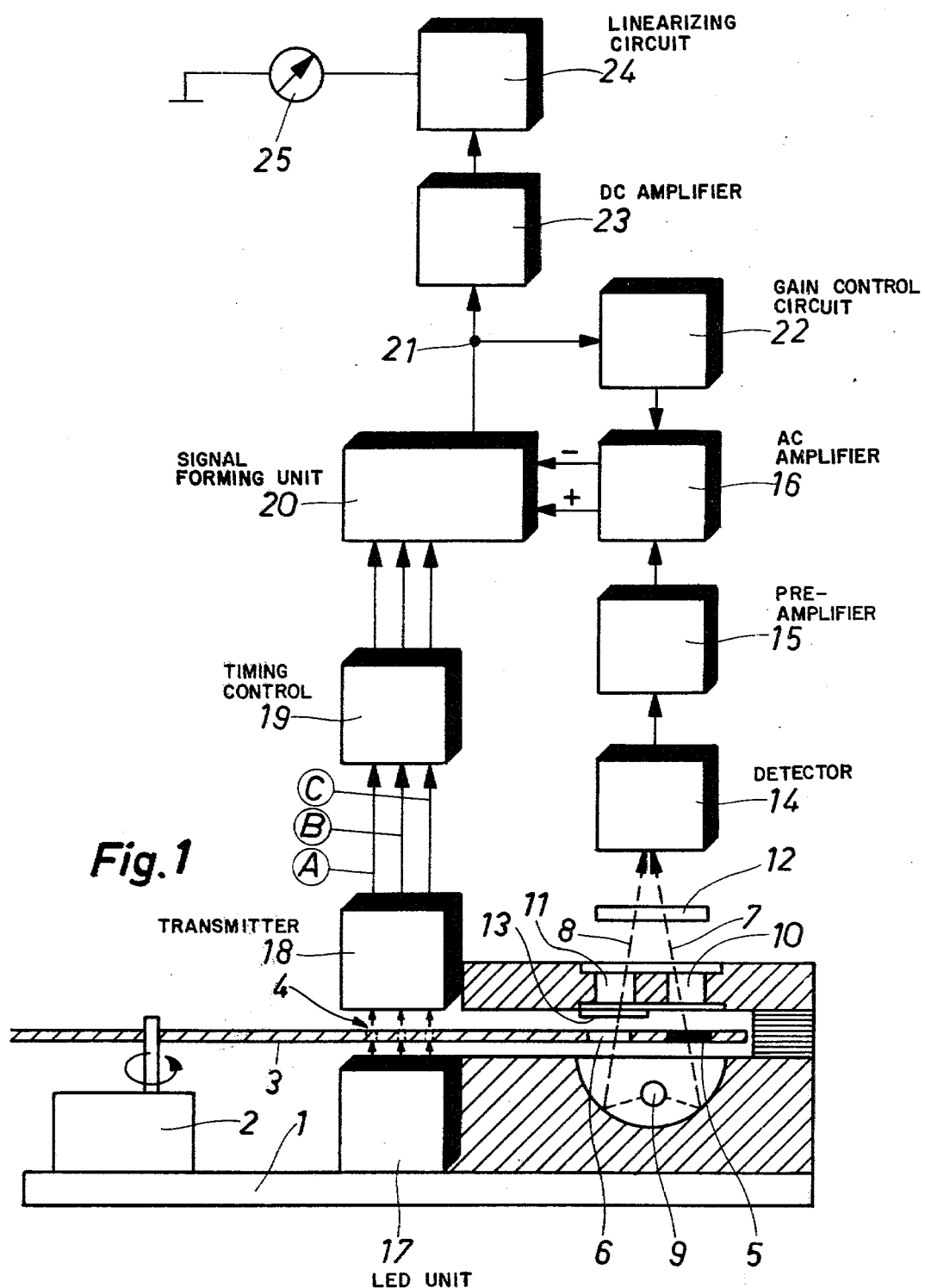
FIG. 1 presents the gas analyzer of the invention, partly as a block diagram and partly in structural cross section presentation.

A motor 2, attached to the frame plate 1, rotates the chopper disk 3 provided with a sequence of holes 5 for chopping the measuring beam 7 and a sequence of holes 6 for chopping the reference beam 8 in such manner that the beams 7 and 8 will alternate. The beams 7 and 8 are transmitted by the infra-red light source 9, and the measuring beam 7 passes through the measuring chamber 10 and the reference beam 8 through the reference chamber 11. In the present exemplary case the analyzer shall be described as a $CO_2$ analyzer. Through the measuring chamber 10 that gas is conducted of which the $CO_2$ content is measured. In the reference chamber 11 a gas has been enclosed from which the $CO_2$ has been drawn off. The filter 12 is employed to leave of the radiation only that wavelength range in which $CO_2$ displays the strongest absorption. After the measuring and reference beams 7 and 8 have in succession arrived at the detector 14, there follows a dark period, which is used towards the automatic gain control to be described later on, by keeping constant the difference between the dark signal and the signal 8 produced by the reference chamber 11. The tripartite signal (measuring signal plus reference signal plus dark signal) thus formed at the detector is conducted through a pre-amplifier 15 to an AC amplifier 16, the operating point of the latter being governed by an automatic gain control circuit 22.

In order to render the said three signals (measuring, reference and dark signal) identifiable and distinguishable from each other, the chopper disk 3 has been provided with three sequences of synchronizing holes 4, through which synchronizing light pulses are transmitted from a LED unit 17, these pulses being received in the light receiver and synchronizing signal transmitter unit 18. The positions of the holes 4 in the chopper disk 3 have been so chosen that the signal A coincides with the measuring signal received by the detector 14, signal B with the reference signal and signal C with the dark signal. With the aid of these synchronizing signals A, B and C the synchronizing and measuring difference signal forming unit 20 is controlled by the timing control unit 19. The unit 20 has the task to form the analog and difference signals between the three different phases of the signal coming from the unit 16. First, therein is generated a reference voltage by measuring the difference between the reference signal and the dark signal. This difference voltage is monitored by an automatic gain control circuit 22 to keep it at a predetermined constant value. The control circuit 22 governs the AC amplifier 16 for maintaining the said, predetermined reference voltage.

Secondly, in the unit 20 the measuring signal proper is formed. This signal is obtained as the difference between the signal received through the measuring chamber 10 and that received through the reference chamber 11. This analog difference signal is conducted to the DC amplifier 23 and thence further over the linearizing and measuring circuits 24 to the display instrument 25, on which the $CO_2$ content can be read. The linearizing process taking place in the circuit 24 serves to compensate for the non-linear relationship between the absorption and the $CO_2$ content in the measuring chamber 10, displayed in FIG. 2.

The above-described principle of design and operation of the analyzer is known in the art. It is unavoidable that the measuring beam 7 travels part of its path through the ambient gas. Hereby the non-linear relationship between absorption and $CO_2$ content, displayed in FIG. 2, introduces the effect that an additional absorption is caused by the ambient $CO_2$ content variations, at comparatively low concentrations already, and which in the gently sloping portion of the curve is large enough to cause an appreciable error in the content that is being measured.

Figure 2:
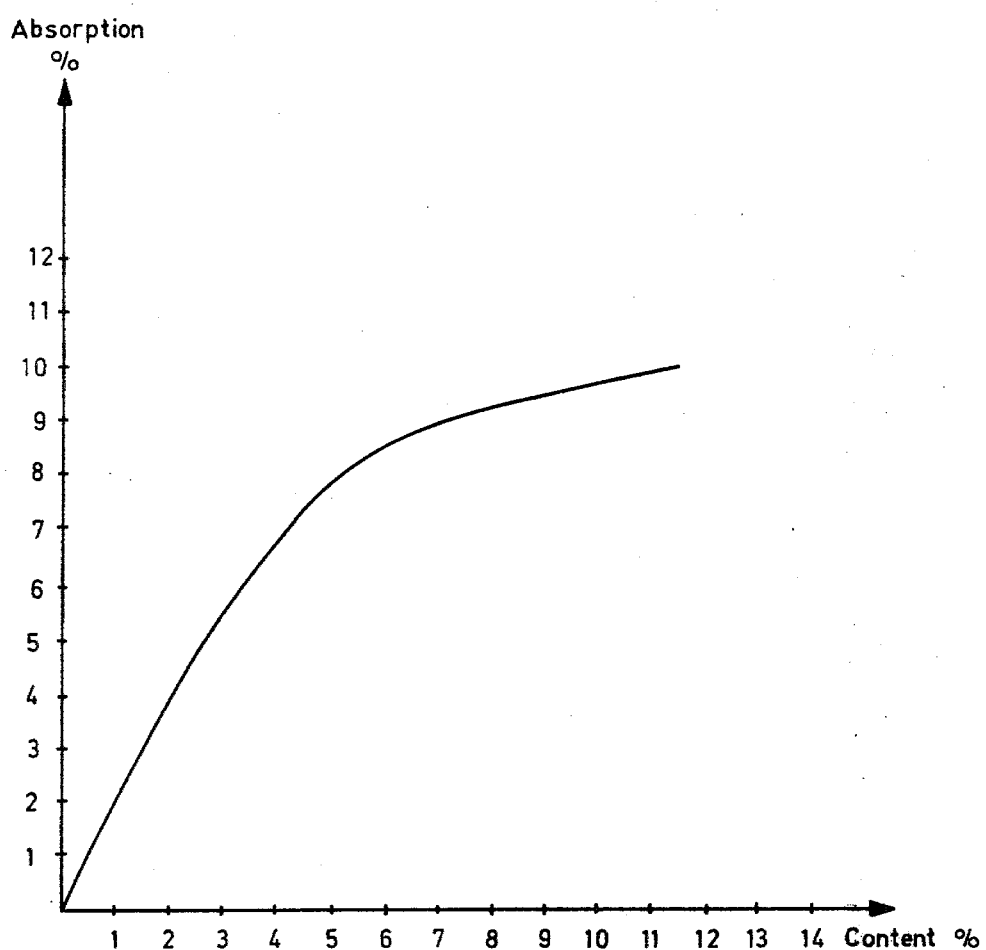
FIG. 2 shows the absorption curve for infra-red radiation plotted over the CO content.

It has been understood in this invention to compensate to a remarkable extent for this error, by placing in front of the reference chamber 11 an attenuation plate 13, which within the wavelength range selected by the filter 12 has a large enough attenuating capacity to cause the result that the automatic gain control circuit 22 shifts the operating point of the AC amplifier 16 to the shallow part of the curve reproduced in FIG. 2. As can be seen in FIG. 2, a suitable absorption for the attenuation disk, in a $CO_2$ analyzer, is about 8%. In that case the additional attenuation due to the ambient environment is sufficient at the reference level, too, to cause such a change of the gain that this change will compensate for a substantial part of that interference attenuation which the measuring beam suffers due to the environment.

This compensating effect is illustrated by the aid of the test examples following below. In both experiments which were carried out, the ambient $CO_2$ content was first 0.0 and, next, 0.3% by volume. The length of the light beam path through ambient air was 4 mm and the path within the measuring chamber, 4 mm. The gas which was measured had in both instances a content of 8% $CO_2$ by volume.

1. Without attenuation disk

| Ambient content, % $CO_2$ | Measuring chamber attenuation | Ambient attenuation | Total attenuation in ref. chamber | Total attenuation in meas. chamber | Equivalent to $CO_2$-% | Total error, $CO_2$-% |
|---|---|---|---|---|---|---|
| 0 | 9.2 | 0 | 0 | 9.2 | 8 | 0 |
| 0.3 | 9.2 | 0.5 | 0.5 | 9.65 | 9.2 | 1.2 |

2. With attenuation disk
Absorption of the attenuation disk is 8%

| Ambient content, % $CO_2$ | Measuring chamber attenuation | Ambient attenuation, % | Attenuation disk, % | Total attenuation in ref. chamber | Total attenuation in meas. chamber | Equivalent to $CO_2$-% | Error, $CO_2$-% |
|---|---|---|---|---|---|---|---|
| 0 | 9.2 | 0 | 8 | 8.0 | 9.2 | 8 | 0 |
| 0.3 | 9.2 | 0.5 | 8 | 8.46 | 9.65 | 8.2 | 0.2 |

From the foregoing, the conclusion can be drawn that, by using an attenuation disk 13 according to the invention, it has been possible in a simple and inexpensive way to substantially improve the accuracy of measurement of the analyzer by causing such a shift of the reference level which moves the operation of the analyzer into the gently sloping part of the absorption curve, whereby the effect of the incremental attenuation due to the ambient environment will produce an adequate change in the amplifier gain for substantial compensation of the incremental attenuation of the measuring beam due to ambience.

Although in the foregoing the invention has been described in association with a $CO_2$ analyzer, it is fully obvious that it is applicable in all and any types of gas analyzers. Among other things the invention has been tried out in an oxygen analyzer, and there too it has been found to eliminate the ambient interference effects to a remarkable extent.

We claim:

1. A gas analyzer, in particular a $CO_2$ analyzer, comprising a measuring chamber for the gas to be examined, a reference chamber from which the gas to be measured has been drawn off, a light source, and a chopper disk to chop the light beam so that the beam alternatingly passes through the measuring and reference chambers and generates a related measuring signal and a reference signal and a dark signal, signal processing means for detecting the difference between said signals, an automatic gain control circuit connected to said signal processing means to maintain constant the difference between the dark signal and the reference signal from the reference chamber, a linearizing circuit connected to said signal process means for compensating for the non-linearity of the difference between the measuring signal and the reference signal, and an attenuation member disposed in the path of the light beam passing through the reference chamber and which in the wave length range employed has a high enough attenuation capacity to cause a shift of the operating point of the gain control circuit so that the linearizing circuit operates at the gently sloping part of the absorption versus concentration curve.

2. The gas analyzer of claim 1, wherein the attenuation member is disposed between the reference chamber and the chopper disk.

3. The gas analyzer of claim 1, wherein the attenuation member is a plate affixed to the surface of the reference chamber.

4. A method of analyzing gas, comprising the steps of locating a first gas having a gas component to be analyzed in a measuring chamber, locating a second gas from which the gas component to be analyzed has been removed in a reference chamber, passing a light beam alternately through the measuring chamber and the reference chamber to alternately generate a measuring signal and a reference signal and a dark signal, maintaining the difference between the reference signal and the dark signal at a constant value by a gain control circuit, linearizing the difference between the measuring signal and the reference signal by a linearizing circuit, and attenuating the light beam passing through the reference chamber to cause a shift of the operating point of the gain control circuit, so that the linearizing circuit operates at the gently sloping part of the absorption versus concentration curve.

5. The method of claim 4, wherein the step of chopping the light beam comprises the step of contacting the light beam with a rotating chopper disk.

* * * * *